United States Patent
Cheng et al.

(10) Patent No.: US 6,808,530 B2
(45) Date of Patent: Oct. 26, 2004

(54) MEDICAL DEVICE FOR TREATMENT OF A GAP OR DEFECT IN THE CENTRAL NERVE SYSTEM

(75) Inventors: Henrich Cheng, Taipei (TW); Lars Olson, Lidingö (SE)

(73) Assignee: Karolinska Innovations AB, Stockholm (SE)

(*) Notice: Subject to any disclaimer, the term of this patent is extended or adjusted under 35 U.S.C. 154(b) by 271 days.

(21) Appl. No.: 09/770,460

(22) Filed: Jan. 29, 2001

(65) Prior Publication Data

US 2001/0017138 A1 Aug. 30, 2001

Related U.S. Application Data (62) Division of application No. 09/230,509, filed as application No. PCT/SE97/01311 on Jul. 24, 1997.

(30) Foreign Application Priority Data

Jul. 26, 1996 (SE) .............................................. 9602879

(51) Int. Cl.⁷ .............................................. A61B 17/08
(52) U.S. Cl. ....................................... 606/152; 128/898
(58) Field of Search ................................. 606/152, 155

(56) References Cited

U.S. PATENT DOCUMENTS

| | | | | |
|---|---|---|---|---|
| 3,786,817 A | * | 1/1974 | Palma | 606/152 |
| 3,833,002 A | * | 9/1974 | Palma | 606/152 |
| 4,669,474 A | * | 6/1987 | Barrows | 606/152 |
| 4,759,764 A | * | 7/1988 | Fawcett et al. | 623/1.1 |
| 4,963,146 A | * | 10/1990 | Li | 428/315.5 |
| 4,966,144 A | * | 10/1990 | Rochkind et al. | 607/89 |
| 5,584,885 A | * | 12/1996 | Seckel | 623/11.11 |
| 5,834,029 A | * | 11/1998 | Bellamkonda et al. | 424/570 |

FOREIGN PATENT DOCUMENTS

| | | |
|---|---|---|
| WO | WO 88 06871 | 9/1988 |
| WO | WO 90 05552 | 5/1990 |
| WO | WO 94 00494 | 1/1994 |

\* cited by examiner

*Primary Examiner*—Gary Jackson
(74) *Attorney, Agent, or Firm*—Young & Thompson (57) ABSTRACT

A medical device (1) of a biocompatible material for use in the treatment of a gap or defect in the central nervous system, which device has a proximal end (5) and a distal end (6) comprising openings (7). The device is adapted to enable connection of nerve fibers of gray and white matter between the proximal end (5) and distal end (6) thereof in predetermined openings (7). The device is of a substantially cylindrical form, or a substantially flat or plate like form and is made of plastic. The openings (7) in at least one end (5, 6) bear distinctively different indicia thereby to indicate whether nerve fibers of gray matter or nerve fibers of white matter are to be inserted therein.

1 Claim, 9 Drawing Sheets

| Bridge number | Intended function |
|---|---|
| 1 | dorsal corticospinal tract (crossed fibers) |
| 2 | rubrospinal tract |
| 3 | central grey matter & formatio reticularis |
| 4 | central grey matter & formatio reticularis |
| 5 | ventral corticospinal tract (uncrossed fibers) and other tracts (VST,RST) |
| 6 | ventral corticospinal tract (uncrossed fibers) and other tracts (VST,RST) |
| 7 | fasciculus gracilis |
| 8 | fasciculus gracilis |
| 9 | fasciculus gracilis |
| 10 to 18 | as above on the other side |

| Treatment | Rat nb | Planned survival time (months) | Open field walking score at sacrifice | HRP tracing result | |
|---|---|---|---|---|---|
| | | | | retrograde* | anterograde† |
| Full repair strategy | 1 | 12 | 3 | 817/1412 | |
| | 2 | 9 | 1 | 0/840 | |
| | 3 | 3 | 3 | 4048/2533 | |
| | 4 | 3 | 2.5 | | +++ |
| | 5 | 3 | 2 | | + |
| | 6 | 1 | 2.5 | | (+) |
| | 7 | 3 | 3 | | + |
| | 8 | 3 | 3 | | + |
| Full repair except aFGF | 9 | 12 | 0 | 0/56 | |
| Repair with white-to-white bridges | 10 | 6 | 0 | | − |
| | 11 | 9 | 0 | 0/2 | |
| Spinal cord transection at Th8 (no cord tissue removal) | 12 | 12 | 0 | 0/0 | |
| | 13 | 12 | 0 | 0/8 | |
| | 14 | 12 | 0 | 0/0 | |
| | 15 | 2 | 0 | | − |
| | 16 | 2 | 0 | | − |
| | 17 | 2 | 0 | | − |
| | 18 | 3 | 0 | | − |
| Normal | 19 | | 5 | 21937/21871 | |
| | 20 | | 5 | | +++++ |
| Acute spinal cord transection | 21 | | 0 | 0/0 | |
| | 22 | | 0 | | − |
| Spinal cord colchicin injection at Th8 | 23 | | 0 | 0/0 | |

*Cells in motor cortex/ cells in brain stem. †Labelled tracts and cells were seen in the bridges and in the distal cord to T11 (+), to T12-L2: +, to L5-S1 +++ Normal +++++

MEDICAL DEVICE FOR TREATMENT OF A GAP OR DEFECT IN THE CENTRAL NERVE SYSTEM

This application is a division of co-pending application Ser. No. 09/230,509, filed on Mar. 1, 1999. application Ser. No. 09/230,509 is the national phase of PCT International Application No. PCT/SE97/01311 filed on Jul. 24, 1997 under 35 U.S.C. §371. The entire contents of each of the above-identified applications are hereby incorporated by reference.

The present invention relates to a medical device of a biocompatible material for use in the treatment of a gap or defect in the central nervous system.

Treatment that promotes functional regeneration across a complete spinal cord transection in man does not exist. In animal experiments (1), recovery after incomplete spinal cord lesions has been achieved in adults treated with myelin-associated protein antibodies while recovery after complete lesions has been demonstrated in neonates (2).

Various attempts have been made over the years to find a replacement for direct nerve stump to nerve stump suturing. Much research has focused on the use of channels or tubular prostheses which permit the cut ends of the nerve to be gently drawn into proximity and secured in place.

All prostheses produced so far are intended for peripheral nerves such as U.S. Pat. Nos. 3,833,002, 4,759,764, 4,870,966 and SE 457 598.

The present inventors have now found that mobility can be restored in rats having complete spinal cord gaps. The gaps have been bridged with multiple intercostal nerve grafts redirecting specific pathways from white to grey matter, and the grafted area stabilised by acidic fibroblast growth factor-containing fibrin glue and compressive wiring of posterior spinal processes: Nerve bridges were created between the peripheral nerves and the spinal cord.

It has also turned out that motility can also be resored under certain circumstances when grafting white to white and grey to grey mass if special antibodies are given to the person being treated or incorporated into inserted material connecting the gap ends of the spinal cord.

The invention relates to a medical device of a biocompatible material for use in the treatment of a gap or defect in the central nerve system comprising one or more means containing connections such as holes or channels arranged for receiving nerve growht promoting materials or substances, which device has a proximal and a distal end area comprising openings from the connections, characterized in that the device is marked and arranged for coupling nerves from the grey and white matter of the central nervous system at the proximal end to certain marked areas in the proximal end area and nerves in the grey and white matter at the distal end to certain marked areas in the distal end area.

The device may be marked and arranged for coupling nerves from the grey matter of the central nervous system at the proximal end to nerves in the grey matter at the distal end and nerves in the white matter of the central nervous system at the proximal end to nerves in the white matter at the distal end. This is especially the case when antibodies are administrated in ordr to promote the nerves to grow together.

In a preferred device according to the invention the device or the means is marked and arranged for redirecting nerves from the grey matter of the central nervous system at the proximal end to nerves in the white matter at the distal end and nerves in the white matter of the central nervous system at the proximal end to nerves in the grey matter at the distal end.

The device can be used in the treatment of complete or partial gaps or defect in the central nervous system. It may consist of one or more means comprising holes or channels arranged for receiving nerve growth promoting materials or substances, which device has a proximal and a distal end area comprising openings from the holes or channels. The openings and/or the end areas may be marked for easily coupling nerves in the grey matter of the central nervous system at the proximal end of the gap to nerves in the white matter of the central nervous system at the distal end and nerves from the white matter in the distal end to nerves in the grey matter of the proximal end.

The expressions proximal and distal refer to direction to and from the head respectively of the individual receiving the transplant.

Preferably the device redirects descending motor pathways from proximal white to distal grey matter, and ascending pathways from distal white to proximal grey matter.

The device may consist of one means that has a substantially cylindrical form comprising channels bridging openings in a first part of the area of the proximal end and openings in a second part of the area of the distal end and channels bridging openings in the second part of the area of the proximal end and openings in the first part of the area of the distal.

The end area can have any suitable form and be planar or non planar such as curved or spherical.

In another embodiment of the invention the device may comprise one or more means having a substantially flat or plate like form. Tubes of biocompatible or biodegradable material containing growth promoting material and/or Schwans cells and/or one or more peripheral nerves are threaded through the holes of the plate or plates. When using a nerve fibre or bundles of nerve fibres the tubes may not be needed.

It is preferred to use as many fine nerves as possible. In the experiment with rats described below 18 peripheral nerves were used to bridge one gap of the spinal cord. It has turned out that it is possible to use even more nerves. Therefore it is postulated that upp to 200 nerves may be used on humans, such as 25–150, preferably 50–100 nerves.

It is also possible to use a device having one or more means with substantially cylindrical form and one or more means having a substantially flat or plate like form. One means with cylindrical form can be surrounded by one or more means with plate like form.

The means may also be one or more tubes of a biocompatible material to be filled with the growth promoting substance and put in place in the spinal cord. The invention also relates to the use of such tubes. The device and means may also have other forms and can e.g. be moulded to suit the subject to be treated When plates only are used they may be threaded with bundles of nerves or with tubes of the biocompatible material filled with the growth-promoting substance. Thus the device may also comprise one or more plates and tubing to be filled when used.

In order to facilitate the redirection of the grey and white matter, the areas of the proximal and distal ends respectively of the means are divided in a first and a second part. The first and the second areas may have any form. It is possible to simply divide the end area in two parts, that may be of the same or of different size. Preferably the first area is a central area and the second area is a peripheral area situated substantially around the central area. It is however also possible that the areas have one or more parts thereof intermingling or sticking into each other with or without connection(s) to the main part area.

Preferably the device consist of one cylindrical means having a first peripheral part and a second central part of the proximal and distal end area connected to the white and grey region respectively of both ends of the gap. Channels going from the peripheral part of one end are being redirected to end up in the central part of the other end of the cylinder and vise versa.

In order to enhance long distance regeneration it is preferable to let one or more channels or bundles of nerve fibres pass the gap and insert the end of the nerves or channels further down the spinal cord. Therefore the device or the means may have some of the channels ending at the side area and not at the distal end area. For example a nerve is introduced in the white matter of the proximal end of the gap and led through a channel that opens up in the side area of the device. It is then introduced through the white matter further down beyond the gap into the grey matter.

Figure 1A:
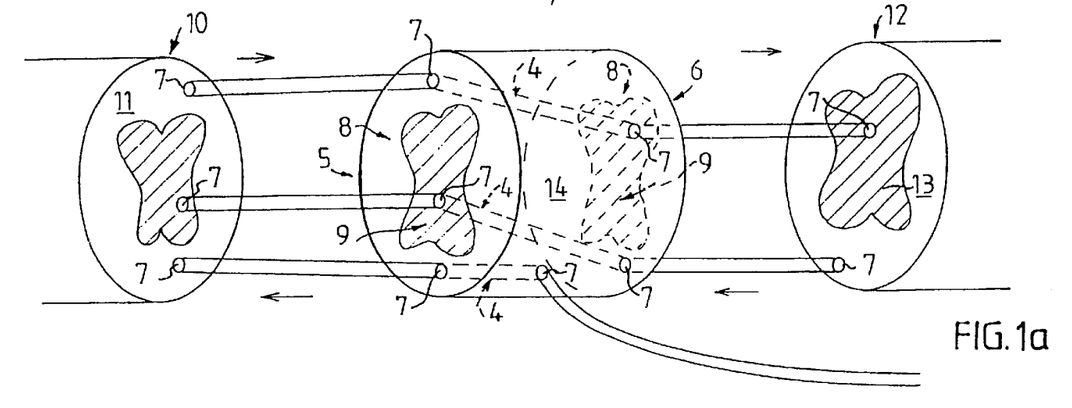
FIG. 1a is a perspective view of one embodiment of the invention and the ends of the central nervous system at a gap, where the pathways in the central nerve systen are redirected.
Figure 1B:
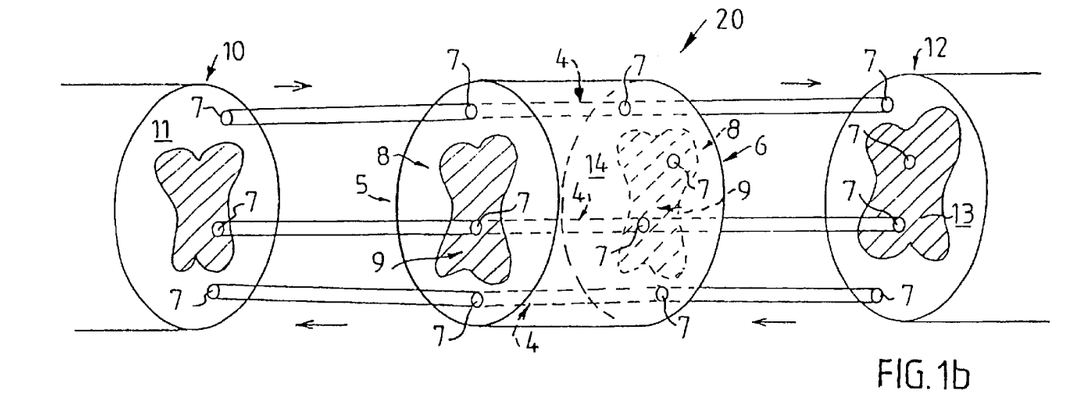
FIG. 1b is a perspective view of another embodiment of the invention where the pathways are recoupled from white to white and from grey to grey mass.

The means of the device may be marked. The first part of the proximal end area may be marked in the same way as the first part of the distal end area as is shown in FIGS. 1a and 1b.

When the device comprises one cylindrical means the first (peripheral) part of both end areas can be marked in a different way from the second (central) part, e.g. white and grey to correspond to the colours of the spinal cord. Marking may not be needed when the device has a transverse end area and first and second parts of the same size as the white and grey zones of the transverse area of the spinal cord.

Figure 2:
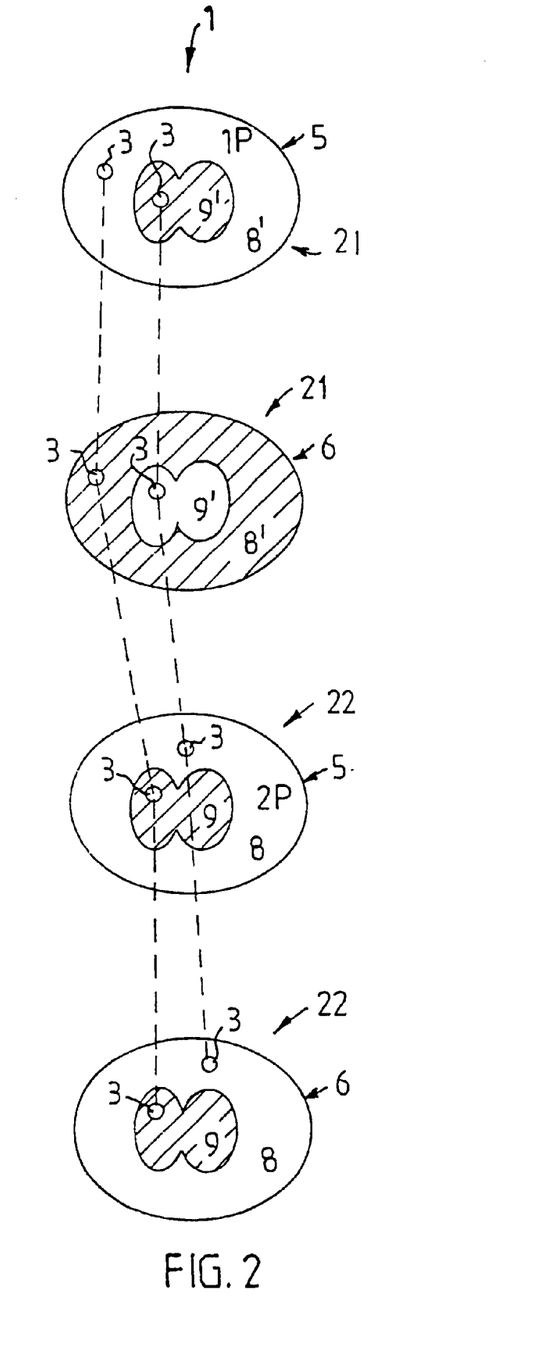
FIG. 2 is a view from above of a device according to the invention consisting of two plates.

In another embodiment the first part of the proximal end area of a means is marked in the same way as the second part of the distal end area and the second part of the proximal end area is marked in the same way as the first part of the distal end area as is means 21 in FIG. 2. This marking may be practical when only one plate is used. It is, however, also possible to use one or more plates without marking them.

The grey matter lies in the centre of the spinal cord in the form of a thick H or a butterfly surrounded by the white matter. There will be less crossing over of bundles of nerves or of channels if the first and second areas are more or less in conformity with the pattern of white and grey matter respectively in the CNS. Moreover there will be still less crossing over if the switches between the different areas take place in the same halves or region of the cross section of the means. Thus, the switches are especially made in the same left (FIG. 4E) or right side region of the spinal cord.

Figure 4A:
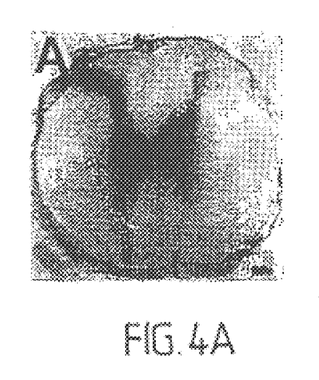
Figure 4B:
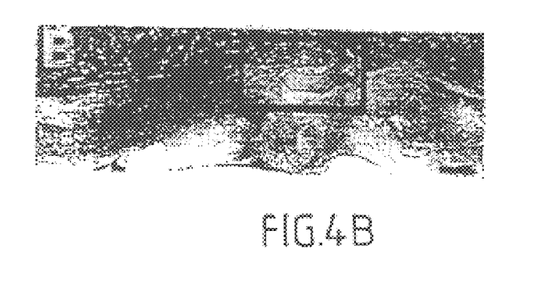
Figure 4C:
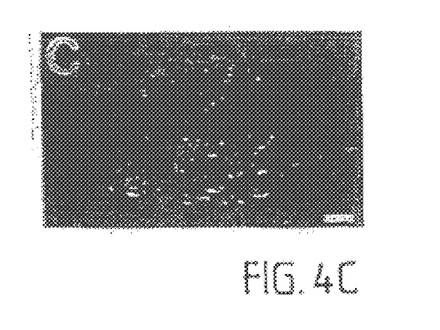
Figure 4D:
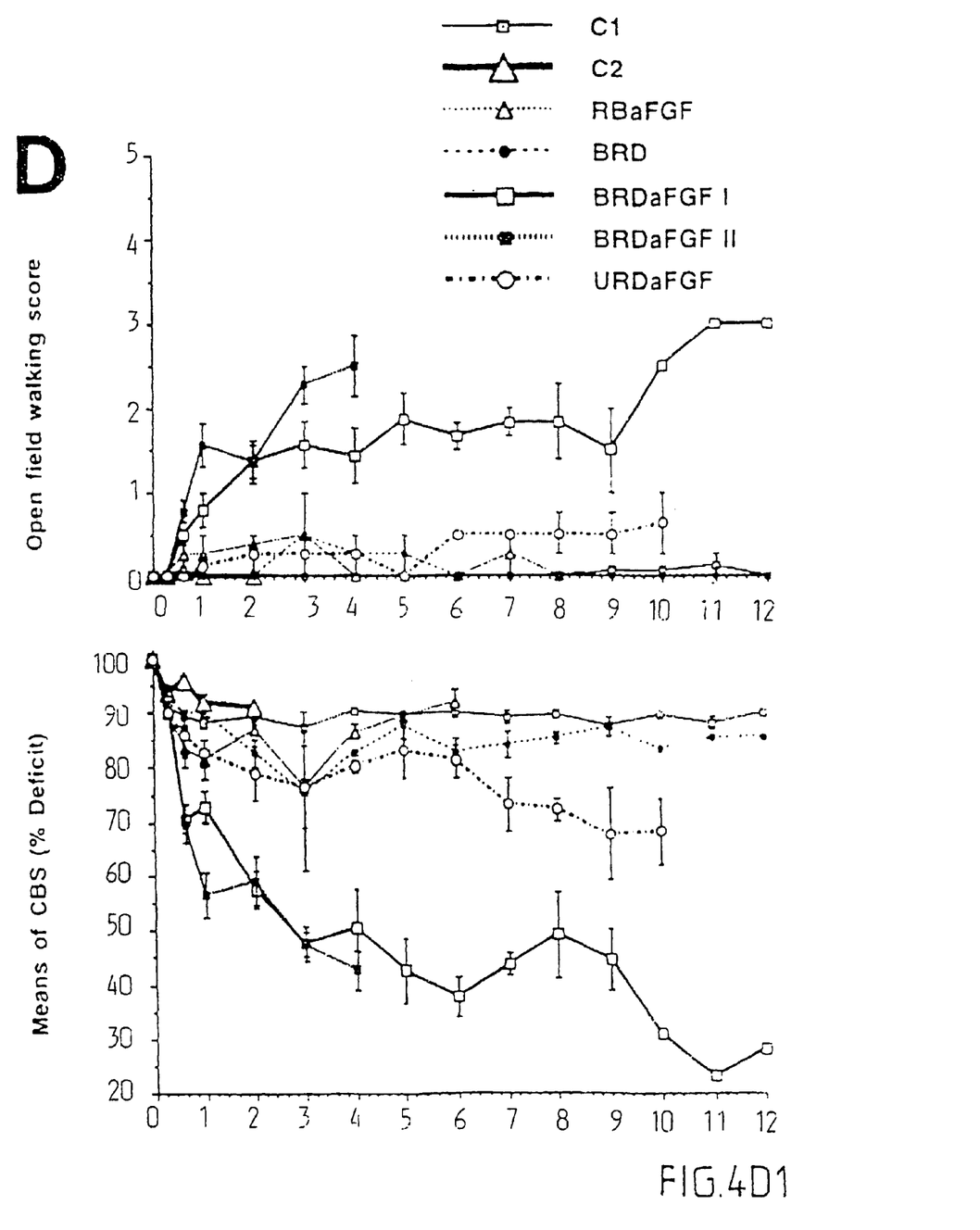
Figure 4D:
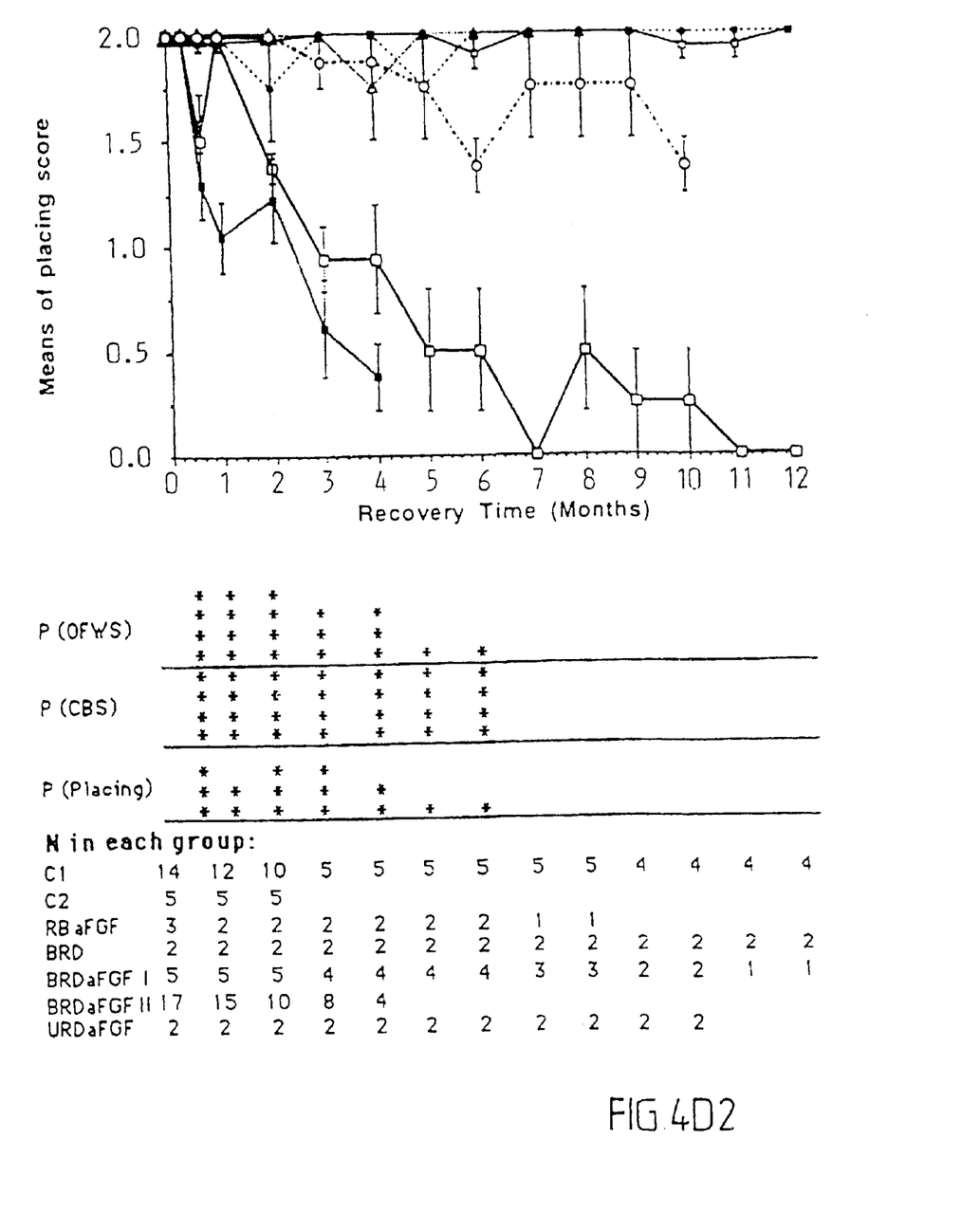
Figure 4E:
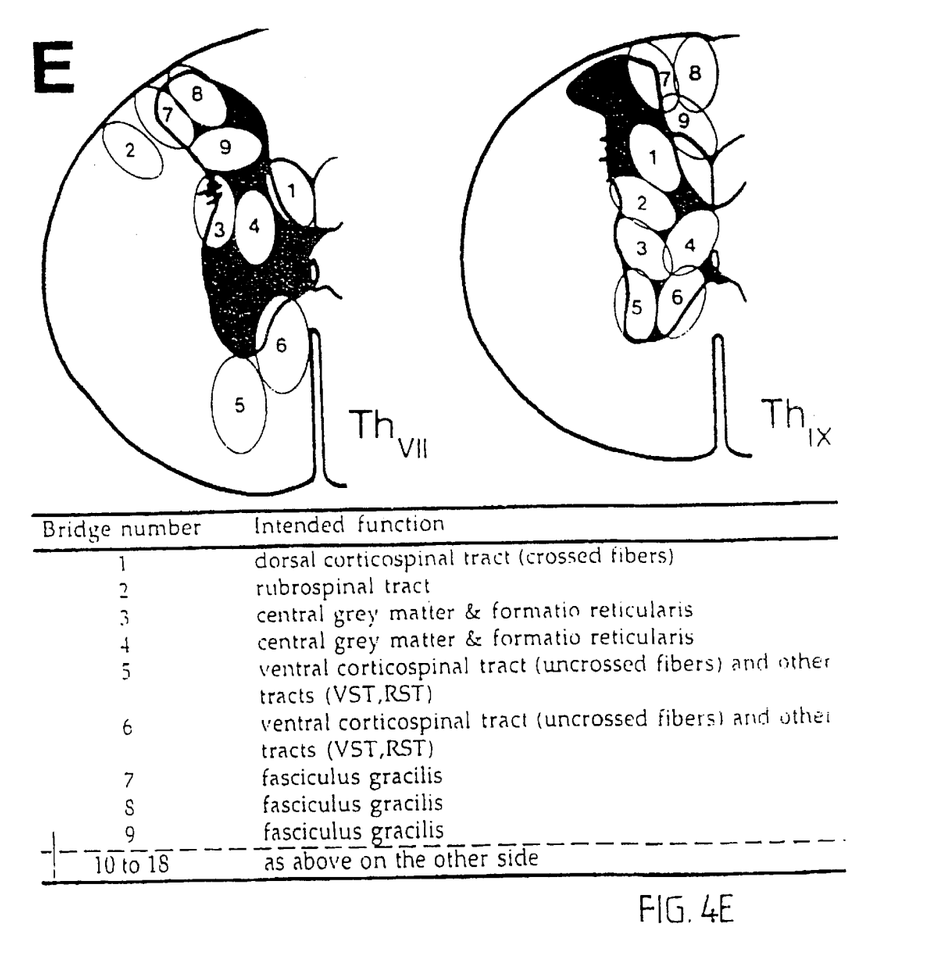

The device may be marked e.g. by a vertically directed line (e.g. when the device has a plate like form) or an area (e.g. when the device has a cylindrical form) in order to make the switches from white to grey matter in substantially the same left or right part of the spinal cord as was done in the rat experiment (FIG. 4E).

When two means in the form of plates are used they may be arranged as follows. A first plate is intended to be placed near the proximal end of the gap and a second plate is to be placed near the distal end of the gap. The proximal and distal end area of the first and second plate has differently marked first and second parts e.g. a white first area and a grey second part in both plates (see FIG. 3). The openings in the first part of the distal end area of the first plate and the openings of the second part of the proximal end area of the second plate are marked with figures e.g. 1 to n. The openings in the second part of the distal end area of the first plate and the openings of the first part of the proximal end area of the second plate are marked with different figures e.g. n+1 to n+m.

The marking may be in the form of different biocompatible colouring substances or different patterns.

According to the invention it is also possible to combine redirecting white to grey mass with direct coupling white to white and grey to grey mass using special antibodies. Such a device may contain isolated areas in the first part marked in the same way as the second part and vice versa, in order not to redirect only some nerves that are coupled to the isolated areas using the antibodies.

The growth promoting material may be any pharmaceutical acceptable material or substance making the grey or white matter preferably the white matter growing. It may be a nerve growth enhancer such as for example a growth factor or active analogue, fragment or derivative thereof. One or more fibres, such as a bundle of numerous fibres or axons of a peripheral nerve and/or Schwans cells may be used. The nerves may be both monofascicular and polyfascicular. Also mixtures of the above mentioned materials and substances can be used possibly together with a glue, that does not negatively affect the growth of nerves. The material may come from the individual to be treated or from other individuals from the same or some other species.

Preferably nerves coming from the ribs such as intercostal nerves are taken out from the individual to be treated and cut into pieces. These nerve pieces or parts thereof are inserted in the holes or channels in the device. It is preferred to have as many nerves as possible as more and better functions are likely to be restored the more bridges that are created. One can use 1 to 100, preferably 9 to 75 especially 15 to 40 bundles of nerve fibres.

The holes and the channels may have any transverse cross sectional form such as round, oval or square. They are preferably general tubular with round or oval lumen. The diameter may be from 1 $\mu$m to 5 mm. Preferably visible bundles of peripheral nerve fibres are inserted in the channels that have a diameter of about 0.2 mm–3 mm, especially 0.5 mm–2 mm.

The device can be delivered without any growth promoting material and be used together with e.g. peripheral nerves or Schwans cells from the individual to be transplanted. It is however also possible to deliver the device with a growth promoting material put in place possibly together with pharmaceuticals or substances preventing microbial and immunological influence on the material during transport and storage or in the patient body. The device may also contain growth factors such as bioactive neotrophic factors e.g. aFGF incorporated into the material of the device or in the holes and/or channels. The growth factor may be present in a gradient concentration that may increase in the proximal or distal direction.

Different gradients can be used for the space holding nerves coming from the white and grey matter respectively.

The device and the means may have any form. The transverse sectional area may for example be round, oval, square or rectangular. Preferably it has about the same form and area as the transverse section of the gap in the spinal cord of the individual receiving the implant. The size of the individual affects the size of the spinal cord. Further the spinal cord is thicker in the regions where the nerves to the arms and legs come out. It is also possible to treat a complete or partial gap. Taking this into account, and with regard to the fact that the means may be plate like or have the form of a cylinder, the device may be produced in different sizes. The length in the direction of the spinal cord may be about 0.2 cm to 5 cm, preferably 0.5 cm to 4 cm. The length of the device is depending on the length of each means that it is composed of. The transversal area of the device and means may vary from about 0.3 cm$^2$ to about 4 cm$^2$.

The invention also relates to a method for restoring a deficiency in the spinal cord on humans comprising filling a device of a biocompatible material with nerves and/or Schwans cells, possibly aslo growth promoting material and possibly also a biocompatible glue and connecting white to grey mass of the spinal cord. When special antibodies are used it is also possible to couple the nerves from white to white mass and from grey to grey mass.

It is also possible to combine the two different ways of coupling the mass of the central nerve system and couple some of the nerves to the same sort of mass (i.e. white to white and grey to grey) and some other nerves from white to grey.

The device may be composed of any biocompatible material such as, for example, polyethylene vinyl-acetate (EVA); or of biocompatible hydrogels, such as polyvinyl pyrolidone, polyethylene oxide (PEO), polyurethanes, acrylates, or mixtures thereof. Preferable acrylates include methacrylates or hydroethylmethacrylates.

Alternatively it may be composed of a bioresorbable, or bioabsorbable biocompatible polymer, such as a polyanhydride, polyester, or mixtures thereof; Poly-alpha-hydroxy acids (PGA); polylactic acid, copolymers of lactic and glycolic acids, and said polymers copolymerized with other polyesters such as epsilon-caprolactone; copolymers having a glycolic acid ester and triethylene carbonate linkages, e.g. the copolymer in the MAXON (American Cyanamid Company, Wayne N.J. 07470, U.S.A.) suture; polydioxanone; polyesters formed from diols and succinic and/or oxalic acid, isomorphic copolyoxalates and poly (alkylene) oxalates; polymers made from unsymmetrically-substituted 1.4-dioxane-2.5-diones.

One can also use silicone, connective tissue fibres such as collagen, polyglycolic acid, composite made of collagen and glycosaminoglucan (see U.S. Pat. No. 4.280,954).

The material of the device is preferably permeable to body liquids and substances in order to facilitate e.g. blood vessels to growing into the device. The material shall have qualities in order to hold and keep the nerve fibres in place. Connective tissue fibres such as collagen are suitable.

The device may be produced by using flexible tubes around which the biocompatible material is moulded. The flexible tubes are bent to change the direction of the channels from the first area of the proximal end to the second area of the distal end and vice versa to create channels changing direction from white to grey matter. The tubes are then drawn out from the device.

Devices, such as plates intended for changing the direction from white to grey outside the means or between the means, can be produced as described in WO 90/05552.

The device is preferably delivered with a thread inserted in the channels. When used, bundles of nerves are tied to the thread and drawn through the channels.

When used the device comprising nerve bundles or channels of biocompatible material containing Schwans cells and/or other nerve growth promoting material are treated with a biocompatible glue containing one or more growth factors.

The glue to be used according to the invention is preferably a fibrin glue containing 50–200 mg/ml, preferably 100 mg/ml of fibrinogen and 0.2 $\mu$g-20 $\mu$g per ml especially 1 $\mu$g-5 $\mu$g per ml, especially 2.1 $\mu$g/ml of aFGF (acidic fibroblast growth factor).

The fibrin glue may be a fibrinogen based compound with double sealant components (Beringplast R P, Behring, Behringwerke A G, Margburg, Germany), containing a vial A with fibrinogen concentrate consisting of 115–232 mg dry substance, containing a human plasma protein fraction with 65–115 mg fibrinogen and a human plasma protein fraction with a factor XIII activity of 40–80 U, and a vial B with aprotinin solution consisting of 1 ml solution containing 1000 KIU bovine lung aprotinin and a vial C of thrombin consisting of 4.9–11.1 mg dry substance containing a human plasma protein fraction with a thrombin activity of 400–600 IU and a vial D with a calcium chloride solution consisting of 2.5 ml solution containing 14.7 mg calcium chloride $2H_2O$ (40 mmol).

The advice of the supplier is followed and the aFGF is added to the vial A when used.

BRIEF DESCRIPTION OF THE DRAWINGS

The invention will now be described with reference to the figures of which:

FIGS. 4 A–F show the results from grafting of rat spinal cord, 4 A–C show microphotographs illustrating stainings of sections through spinal cord segments, 4D hindlimb function, 4E schematic illustration of white-to-grey matter nerve bridges and 4F summary of data from animals

In the device 1a of FIG. 1 the means 2 has the form of a cylinder with a proximal end area 5 and a distal end area 6 having first part 8 and second part 9. The first part 8 and the second part 9 of the proximal and distal ends 5 and 6 are white and shaded respectively. The device contains channels 4 of which three are shown in the drawing. One channel 4 leads from the first part 8 of the proximal end area 5 to the second part 9 of the distal area 6. Another channel leads from the second part 9 of the proximal end area 5 to the first part 8 of the distal end area 6. One of the channels 4 ends in an opening 7 on the side area 14 of the device in order to be shunted passed the distal end of the CNS gap and introduced into the CNS further down at a suitable angle through the white into the grey matter. The channels have been threaded with bundles of nerves (not shown).

The end areas have parts marked in different ways making it easy to see e.g. that channels coming out from the white first part 8 of the proximal end area 5 are to be inserted into the white matter 11 of the end area of the proximal gap 10. Channels coming from the grey second area 9 in the distal end 6 of the device are inserted in the grey matter 13 of the end area of the distal gap 12. Correspondingly other channels coming out from the white first part 8 and grey second part 9 of the end areas 5 and 6 of the device are inserted into the mass of the end areas of the CNS gap having the same colour. With the device of FIG. 1 descending motor pathways from proximal white were coupled to distal grey matter and ascending pathways from distal white to proximal grey matter according to the arrows.

The device of FIG. 1b is intended to be used together with a material such as certain antibodies, that can induce growth in the nerve material. Therefore the pathways need not to be redirected. The device comprises one means 20 in which two channels 4 are shown to lead from the first part 8 of the proximal end area 5 to the first part 8 of the distal end area 6. Another channel 4 is shown to lead from the second part 9 of the proximal end area 5 to the second part 9 of the distal end area 6. Thus, no redirection is made. The device of FIG. 1b may also have channels ending in openings on the side area 14 to be shunted past the gap and introduced into the CNS fierier down (not shown).

FIG. 2 shows the proximal and distal end areas of a device 1 consisting of two means 21 and 22 in the form of two plates with holes 3 through which bundles of nerves or tubes filled with growth promoting material such as Schwans cells may be threaded according to the dashed lines. The proximal and distal ends of the two plates are shown. The plates 21, 22 are marked 1P and 2P respectively in order to be placed in the right order and with the proximal ends towards the head of the patient. The proximal end 5 of the first plate 21 marked "1P" has a white first part 8' and a grey second part 9' to show where to insert the tubes or nerve bundles into the white and grey matter of the proximal CNS gap later on. The distal end 6 of the first plate is marked in order to direct the threading of the nerves coming out of the first plate, the first part 8' being grey and the second part 9' being white. The proximal part 5 of the second plate 22 is marked to receive the nerves from the right part of the first plate in order to change the direction from white to grey. Thus, the first part 8 of the proximal end 5 is white and the second part 9 is grey, the first part 8 and second part 9 respectively of the distal end 6 of the second plate 22 being marked in the same way, white and grey. The plates may change places but in such a case the crossing over from white to grey area will not take place between the plates but after the second plate. When used, glue is placed between the plates and at the site of insert or in the spinal cord.

Figure 3:
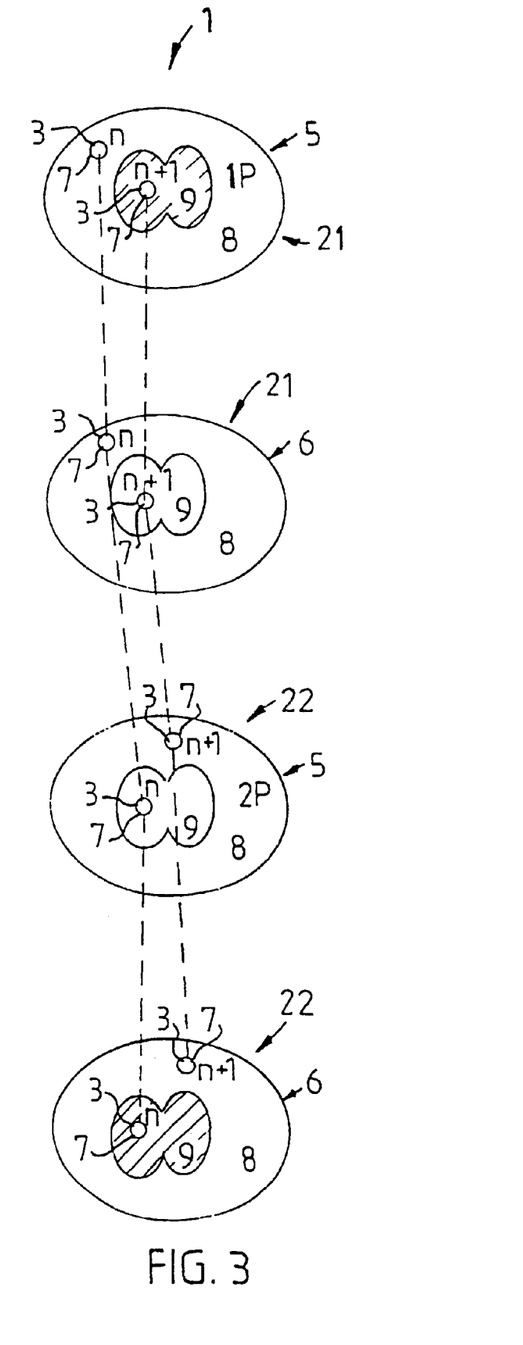
FIG. 3 is a view from above as in FIG. 2 showing possible marking of the plates with figures in order to facilitate the threading of nerves through the plates.

It is also possible to mark the first and second part of the proximal area of the first plate white and grey as in FIG. 2 but instead of marking the areas of the distal end of the first plate and the proximal area of the second plate openings 7 of the holes 3 in these areas may be numbered in order to direct the threading as shown in FIG. 3.

When making and numbering the wholes it is possible to avoid or minimise crossing of the tubes or nerve bundles and to keep the redirection between white and grey matter in the same left or right part of the device and the spinal cord.

Tests Showing Spinal Cord Repair in Adult Paraplegic Rats and Partial Restoration of Hindlimb Function (Science, Jul. 26, 1996, in press)

Complete spinal cord gaps in adult rats were bridged with multiple intercostal nerve grafts redirecting specific pathways from white to grey matter, and the grafted area stabilised by acidic fibroblast growth factor-containing fibrin glue and compressive wiring of posterior spinal processes. Hindlimb function improved progressively during the first 6 months as assessed by two generally accepted scoring systems. The corticospinal tract regenerated through the grafted area to the lumbar enlargement, as did several bulbospinal pathways. Together these data suggest a possible repair strategy for spinal cord injury.

To avoid ambiguities, and to model the most severe clinical scenario. we studied adult rats with complete surgical transection of the spinal cord including removal of 5 mm of the cord at T8. Histology of excised pieces of spinal cord demonstrated complete transection (FIG. 4A). We then proceeded with a repair strategy (3).

We used peripheral nerve implants (4) to bridge the gap in the spinal cord (FIGS. 4B and C and FIG. 5B) and found that multiple fine nerve implants (18 nerves to bridge one gap) gave better precision than the use of fewer thicker nerves. To evade oligodendroglial proteins that inhibit axon regeneration (5), we re-routed regenerating pathways from non-permissive white to permissive grey matter (6). The peripheral nerve bridges thus redirected descending motor pathways from proximal white to distal grey matter, and ascending pathways from distal white to proximal grey matter (FIG. 4E), taking into account the specific anatomy of rat descending and ascending pathways (7). To stabilise the lesioned area and the peripheral nerve bridges, the grafted area was filled with a fibrin-based tissue glue that does not impair nerve fibre growth (8), and fixed the vertebral column in dorsiflexion by wiring (9).

Acidic FGF is a normal spinal cord constituent (10). Lacking a signal sequence, it is thought to be sequestered within cells, and released only after damage. Consequently, FGF may be involved in repair (11). It also decreases gliosis and enhances nerve fibre development in spinal cord grafts (12). Mixing aFGF into fibrin glue allows slow release (13).

Animals were followed over time for signs of functional recovery and rated by two independent blinded observers using the CBS (14) and the OFWS (15). Key responses were video-recorded. Hindlimb function in animals subjected to the five-step procedure improved significantly, beginning three weeks after operation and continuing through the year of observation (FIG. 4D). Animals subjected to unilateral treatment also improved, although to a lesser degree. Four different control groups (14 transection only, 5 cord removal only, 3 white-to-white matter bridging, 2 omissions of aFGF), did not improve (FIG. 4D). Improvement was manifest as appearance of a functional posture in hindlimbs (usually flexion at hips, then knees, then dorsiflexion at ankles). In controls, hindlimbs remained extended and externally rotated. Improvement was symmetrical in 6 cases (28%), and asymmetrical in the rest. Locomotion involved trotting rather than ambling gait (FIGS. 5 H–J). Hindlimbs partially supported body weight and movements were noted in the three major joints. Such movements were not seen in any of the control groups. We also found strongly statistically positive effects on contact placing scores of both groups with fall treatment (FIG. 4D), suggesting that functional recovery involves the corticospinal tract (2).

Figure 4F:
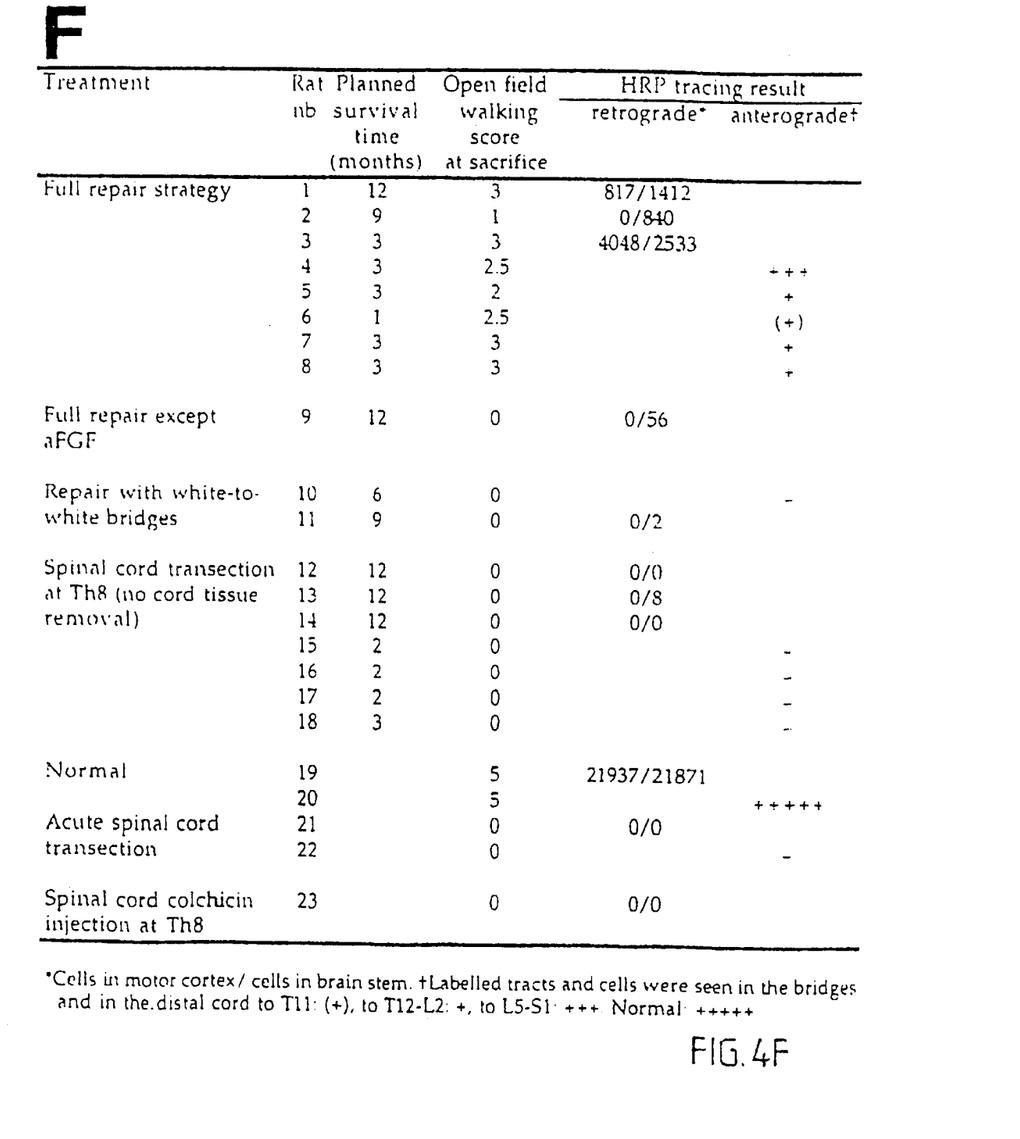

Anterograde wheat-germ agglutinin horseradish peroxidase (WGA-HRP) tracing from the sensorimotor cortices and retrograde WGA-HRP tracing from the lumbar enlargements were used to document fibre tract regeneration (FIG. 1F, 16). The spinal cord and brain were analysed and labelled nerve cell bodies counted (17). Sections from the engrafted area were analysed with cresyl violet or antibodies against neurofilament and glial fibrillary acidic protein (GFAP) to illustrate morphology, nerve fibres in the bridges, and the degree of gliosis. Anterograde tracing is exemplified by one treated animal (FIGS. 4F, 5E, 5F, 5G) with labelled fibres descending in the dorsal funiculus of the proximal stump, traversing the bridging grafts, and reaching grey matter of the proximal portion of the distal stump. Fibres descended at the interface between the dorsal funiculus and dorsal grey matter and ended along the dorsomedial aspect of the dorsal horn in regions adjacent to substantial gelatinosa in the lumbar enlargement. The labelled fibres were thus found in areas corresponding to the pathway of the rat corticospinal tract as shown in rodent cortical ablation studies (7). In the four other animals analysed by anterograde tracing (FIG. 4F), labelled fibres traversed the bridging grafts and were found in grey matter to T11, T11–12, T12 or L1–2. In four transected control animals and in one animal subjected to white-to-white matter bridging plus aFGF, the corticospinal tracts did not reach the distal spinal cord stumps. Anterograde tracing of controls indicated no connections to the distal stumps (FIG. 4F).

Figure 5A:
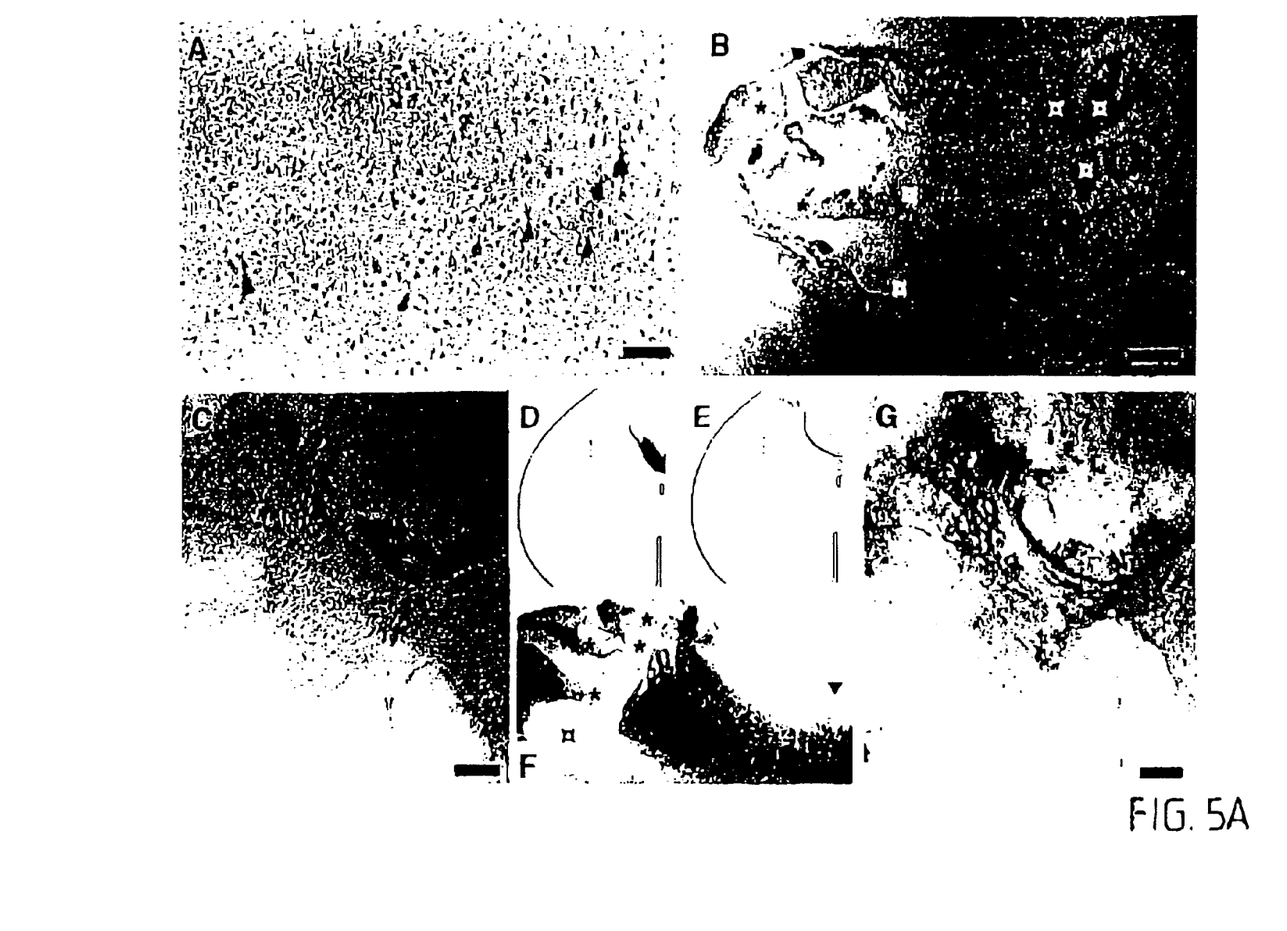
FIGS. 5A and 5B show morphology and sequential videoframes from experimental animals.

Application of WGA-HRP to the lesioned lumbar spinal cord led to labelling of motoneurons in layers III–V of hindlimb motor areas bilaterally in cortex cerebri in two of the three treated animals (FIG. 5A). Labelled neurones were also observed in dorsal tegmentum, the lower limb areas of the red nuclei, reticular nuclei, and raphe nuclei in all treated animals. A few raphe neurones (8 cells) were labelled in one of the three transected controls and one grafted animal without aFGF (56 cells). Numerous raphe neurones were labelled in animals receiving the five-step procedure. Thus a substantial number of regenerating descending axons, including the corticospinal tract and other supraspinal neurones, appears essential for functional recovery. Animals with improvement of hind limb function showed evidence of regeneration of both the motor initiation and the voluntary gait modification circuits to the spinal cord central pattern generator (18), suggesting that these reconnections allowed animals to partially control their hindlimbs. The degree of functional recovery appeared correlated to the degree of regeneration of motor fibre systems (FIG. 4F). GFAP-immunohistochemistry demonstrated large cysts and wide GFAP-poor gaps between the cord stumps ($4.7\pm0.86$ mm, n=5) in C1 controls, whereas animals receiving the full repair strategy had significantly shorter GFAP-poor gaps ($0.7\pm0.19$ mm, n=4; $p<0.001$, ANOVA). The bridge grafts in the latter group displayed rich neurofilament immunoreactivity. Researchers have studied many different models of spinal cord injury in animals. Incomplete spinal cord lesions such as hemisections, contusions, compressions, and different chemical or mechanical partial lesions have generated valuable information about reactive and compensatory changes, but several of these models are less suitable for studies of functional recovery caused by regeneration of cut axons. We have shown that our procedure can lead to a substantial degree of structural and functional recovery in the completely transected adult rat spinal cord, including regeneration of pyramidal tract axons, hindlimb movements and weight support. It remains to be seen to which extent our technique is applicable to the chronic paraplegic state and to humans.

REFERENCES

1. E. Puchala, W. Windle, Exp. Neurol. 55, 1–42 (1977); L. Olson et al., Brain Res. Bull. 9, 519–537 (1982).
2. Y. Iwashita, S. Kawaguchi, M. Murata, Nature 367, 167–170 (1994); L. Schnell et al., Nature 367, 170–173 (1994); B. Bregman, et al., Nature 378, 498–501 (1995).
3. Vertebrae T7–10 were exposed in adult 250-g female Sprague-Dawley rats, under halothane (1.5%) anaesthesia (respiratory rate_60/min, rectal temperature <3° C. below normal). Following T8 and T9 posterior laminectomies and bipolar cauterisation to control haemorrhage, a 5-mm T8 spinal cord segment was removed with microscissors (FIG. 4A). Eighteen intercostal nerves collected in Hanks' were used to reconnect and redirect pathways between the spinal cord stumps (FIG. 4E). The floor of the cavity between the spinal cord stumps was covered by a thin gelfoam layer. Minced pieces of peripheral nerve were used to fill the angle between the gelfoam bottom and the ventral-most (white matter) surface of the cut end of the distal spinal cord stump, producing a slanted floor allowing some physical support of those nerve bridges that went from deep (white matter) proximal sites to somewhat more dorsal (grey matter) distal sites. The cut ends of the intercostal nerve bridges were held against, and attached to the semi-dry spinal cord stump surfaces. The two fibrin glue sealant elements (Beriplast P, generously provided by Behring, Germany) were prepared (see 8 & 13). aFGF (kindly provided by Drs Yihai Cao and Ralf Petterson, Ludwig Institute for Cancer Research, Stockholm) was mixed into the fibrinogen plus aprotinin solution. This solution was mixed with 10 $\mu$l thrombin plus calcium chloride to form an aFGF-containing (2.1 $\mu$g/ml glue) glue cast (final glue volume_ 10 $\mu$l) in the engrafted area. The T7 and T10 spinal processes were fixed in dorsiflexion with an S-shaped monofilament surgical steel (DS-20, Ethicon) loop, fastened to the spinal column with non-absorbable circumspinal threads. In experimental animals, one group was subjected to unilateral redirection and aFGF in the glue (URDaFGF), the other two groups were subjected to bilateral redirection and aFGF glue (BRDaFGF) using autografts (50%) mixed with allografts (I) or only autografts (II). Control animals were subjected to transection at T8 (C1), or removal of 5 mm cord segment (C2), or grafted with the same methods except HBSS replaced aFGF (BRD), or grafted using only white-to-white matter connections (RBaFGF). Animals were caged on thick soft bedding, with heating from below during the first postoperative days. Manual emptying of the bladder was performed twice daily as long as needed. Antibiotics (Borgal, Hoechst, 15 mg/kg, subcutaneously) was injected once daily 7 days. Decubitus sores on hindlimbs were treated with iodine-soaked dressings. Animals were killed if severe sepsis (urinary tract infection), infected decubitus sores, or other wounds occurred. For the major experiments described here, the mortality was less than 10%. Experiments were approved by the animal research ethical committee of Stockholm. Animals were sacrificed at different time points for histological analyses but no earlier than one month after surgery to ensure complete degeneration of cut descending fibres in the distal stump (9).
4. S. David, and A. Aguayo, Science 214, 931–933 (1981); M. Benfey, and A. Aguayo, Nature 296, 150–152 (1982); R. Bunge, Curr. Opin. Neurobiol. 3, 805 (1993).
5. T. Savio, and M. Schwab, Proc, Natl. Acad. Sci. USA 87, 4130 (1990); M. Schwab, TINS 13, 452 (1990).
6. L. Nygren, K. Fuxe, G. Jonsson, L. Olson, Brain Res. 78, 377 (1974); R. Kuang, M. Merline, K. Kalil, Development 120, 1937–1947 (1994).
7. L. Brown, Exp. Brain. Res. 13, 432 (1971).
8. H. Cheng, S. Almstrom, L. Olson, J. Neural Transplant. Plast. 5, 233 (1995).
9. H. Cheng, L. Olson, Exp. Neurol. 136, 149–161 (1995).
10. R. Elde, et al., Neuron 7, 349 (1991); Y. Cao, Thesis, Karolinska Institute (1993); M. Koshinaga, H. Sanon, S. Whittemore, Exp. Neurol. 120, 32 (1993).
11. P. McNeil, L. Muthukrishnan, E. Warder, P. D'Amore, J. Cell Biol. 109, 811 (1989).
12. M. Giacobini, B. Hoffer, G. Zerbe, L. Olson, Exp. Brain. Res. 86, 73 (1991).
13. H. Cheng et al., Exp. Brain. Res. 104, 199 (1995).
14. K. Gale, H. Kerasidis, J. Wrathall, Expt. Neurol. 88, 123 (1985). Percentage functional deficit as indicated by the Combined Behavioral Score (CBS) was used for behavioural evaluation. The CBS (except hot plate), ranging from 100 points (complete paralysis) to 0 (normal), consists of motor score (0–45), toe spread (0–5), righting reflex (0–15), extension withdrawal (0–5), placing reflex (0–5), climbing on inclined plane (0–15), and swim test (0–10).

15. M. Beattie, J. Bresnahan, In: Criteria for the assessment of recovery of function: behavioural methods, M. Brown, et al., Eds. (American Paralysis Association, Springfield, N.J., 1989), pp. 16–25; D. Behrmann, J. Bresnahan, M. Beattie, B. Shah, J. Neurotrauma 9, 197–217 (1992). Open field walking measured the animal's gross locomotor ability during a 5-min testing period. Two coded animals were observed simultaneously to stimulate locomotor activity and scored according to a modified Tarlov scale, ranging from 0 (flaccid paralysis) to 5 (normal walking). This scale was subdivided to more accurately reflect the pattern of recovery of locomotor function as follows: 0, no spontaneous movement; 1, movement that is not reflexive, movement in the hip and/or knee, but not ankle; 2, movement of the limb in all three major joints; 3, active support, uncoordinated gait or occasional short bouts of coordinated gait; 4, co-ordination of forelimbs and hindlimbs in gait (trotting), walks on knuckles or medial surface of foot or few toe drags); 5, normal.

16. L. Heimer, in Neuroanatomical Tract-Tracing Methods, L. Heimer, M. Robards, L. Zaborszky, Eds. (Plenum Press, New York, 1981, 1989). For retrograde HRP-tracing, six 0.1 $\mu$l 5% WGA-HRP (Sigma) injections were made into the lumbar enlargement (L4–5, 25 mm distal to the distal graft-host interface) and combined with an L6 transection to enhance HRP uptake. Positive and negative controls included injection of WGA-HRP with/without colchicin blockage or an acute cut at T8 (FIG. 4F). For anterograde HRP-tracing, a total of 2 $\mu$l 5% WGA-HRP was injected into the sensorimotor cortices using five 0.2 $\mu$l injections per side. Positive and negative controls are also given in FIG. 4F. Animals were perfused 48 hours later (Ringer's solution, 2% paraformaldehyde, 10% sucrose). For immunohistochemistry of grafted areas, tissues were further treated with 4% paraformaldehyde for 2 hours and then with polyvinylpyrrolidone (Sigma) for 6 weeks to allow sectioning of soft and bony tissue together. Cryostat 14-$\mu$m sections for immunohistochemistry and 60-(brain and brainstem) or 90-$\mu$m (spinal cord) free-floating sections for tetramethylbenzidine histochemistry were collected.

17. M. Abercrombie, Anat. Rec. 94, 239 (1946). HRP-labelled neuron counts required presence of the nucleus. The total number of neurones (N) equals n t/(t+d), where n is the number of nuclei of HRP-labelled neurones counted times the section period; t is the section thickness and d the average diameter of counted nuclei.

18. S. Grillner, in Control of Posture and Locomotion, R. Stein, K. Person, R. Smith, J. Redford, Eds. (Plenum Press, New York, 1973), pp. 515–535.

19. We dedicate this paper to Arne Nylander. Supported by APA, the Swedish MRC, USPHS grants, Taiwan Chin-Lin Fund and NSC. We thank the late Jan Arvidsson for valuable tracing advice, and assistance from Susanne Almström, Monica Casserlöv, Kjell Erlandsson, and Ida Engqvist.

Figure Legends:

FIG. 4. (A) Microphotograph illustrating cresyl violet-stained transverse section through removed spinal cord segment. Bar: 250 $\mu$m. (B) Sagittal section of a repaired junction area stained with cresyl violet. Note nerve bridge grafts. Boxed area indicates the redirected fasciculus gracilis (upper) and dorsal corticospinal tract (lower) between the proximal (left) and distal stump (right). Bar: 1000 $\mu$m. (C) Adjacent section immunostained with MAb to neurofilament protein 70,000. Numerous nerve fibres are present in the intercostal nerve bridges. Bar: 200 $\mu$m. (D) Hindlimb function in the 7 different groups (see 3). Hindlimbs were assessed independently (except inclined plane test) to identify asymmetric recovery. Animal scores were generated by averaging hindlimb scores. Open field walking (upper panel) measured the animal's gross locomotor ability during a 5-min testing period. In the treated groups (BRDaFGF I & II), the scores improved significantly more than in the controls (C1+C2) from the third week on (Mann-Whitney). Unilaterally treated animals (URDaFGF) improved to a lesser degree as seen 6 months after surgery. Percentage functional deficit as indicated by the CBS is illustrated in the middle panel. Animals subjected to the five-step procedure improved significantly compared both to animals in which the spinal cord was only transected (C1) and animals with removal of a cord segment (C2, ANOVA). Contact placing score (lower panel) indicates functional recovery of the corticospinal tract and is significantly better in animals subjected to the five-step procedure than controls until 6 months (Mann-Whitney). **: $P<0.0001$; *: $p<0.001$; **: $p<0.01$; *: $p<0.05$. (E) Schematic illustration of white-to-grey matter nerve bridges. Pieces of intercostal nerves were used to reconnect and redirect pathways between the spinal cord stumps, ThVII, ThIX: seventh and ninth thoracic segment). For each redirected tract, one to three intercostal nerves were used. (F) Summary of data from animals in which both open field walking scoring and HRP-tracing data were collected. Ranking tracing results from 0 (negative) to 10 (normal), the full repair animals differ significantly from controls ($p<0.001$, Mann-Whitney).

Figure 5B:
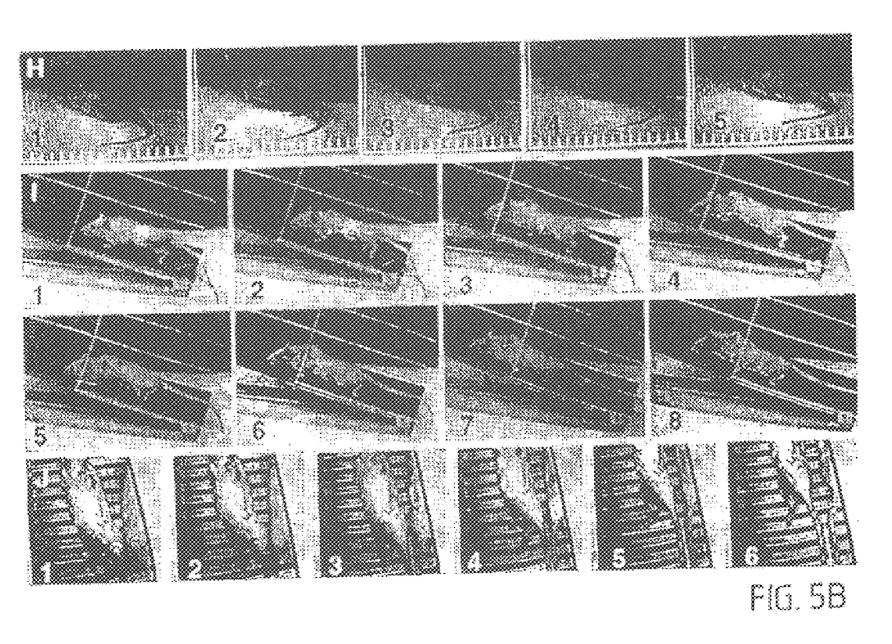

FIG. 5. Morphology and sequential videoframes from experimental animals. (A) Tetramethylbenzidine histocheinistry of cortex cerebri (1 mm posterior to bregma) in a rat one year after the five-step procedure and 48 hrs after retrograde WGA-HRP tracing from the lumbar enlargement. Labelled pyramidal cells are found in the hindlimb motor area. Bar: 100 $\mu$m. (B) Cresyl violet cross-section of bridge area in a treated rat after 4 months. Note 15 nerve bundles (*) and blood vessels (€). Bar: 600 $\mu$m. (C–G) Anterograde transport of WGA-HRP after injection into sensorimotor cortex in a normal rat (C, schematically depicted in D) and a treated rat 3 months after surgery (F and G, schematically depicted in E). Sagittal section of the bridge area (F) shows labelled fibres traversing bridging grafts (*) and reaching the distal stump (right). Some tissue was lost during free-floating processing of section (€). Transverse section of the lumbar enlargement (G) shows labelled fibres in the dorsal funiculus at the white/grey matter interface, and adjacent to substantial gelatinosa. Bar: 200 $\mu$m in C and G, 500 $\mu$m in F. (H–J) Sequential videoframes (interval between each frame: 0.12 sec) of 3 rats subjected to complete five-step procedures. (H) Animal after 3 months. Note that hindlimbs can support body weight during forward stepping. Toe dragging was absent in this animal. (I & J) Rats climbing a 45-degree inclined plane one year (I) or 3 months (J) after surgery. Hindlimbs partially supported body weight and displayed movements in all three major joints. A trotting, rather than ambling or random movement of the four limbs was noted (data not shown), although the hindlimb toes dragged during walking in I.

What is claimed is:

1. A method for restoring a deficiency in the spinal cord of humans comprising the step of bridging spinal cord gaps with multiple intercostal nerve grafts redirecting specific pathways from white to gray matter.

* * * * *